United States Patent
Almasian et al.

(10) Patent No.: US 7,137,974 B2
(45) Date of Patent: Nov. 21, 2006

(54) STERILE CONNECTOR

(76) Inventors: Joseph M. Almasian, 2 Tallard Rd., Westford, MA (US) 01886; Brett M. Belongia, 380 Boxford St., North Andover, MA (US) 01845; Frank Lentine, 7 Cedar Ridge Dr., Bedford, MA (US) 01730; Martin Morrissey, 107 Cabot St. #2, Beverly, MA (US) 01915; Curtis Nauseda, 51 Fairfax St., Apt. 1, Somerville, MA (US) 02144; Chau Nguyen, 11 Spring Garden St., Dorchester, MA (US) 02125; Stephen Proulx, 59 Liberty Square Rd., Boxborough, MA (US) 01719; Naren Renganath, 25 Princeton Rd., Burlington, MA (US) 01803

( * ) Notice: Subject to any disclaimer, the term of this patent is extended or adjusted under 35 U.S.C. 154(b) by 330 days.

(21) Appl. No.: 10/626,282

(22) Filed: Jul. 24, 2003

(65) Prior Publication Data

US 2005/0090797 A1    Apr. 28, 2005

(51) Int. Cl.
*A61M 1/00* (2006.01)
*F16L 37/28* (2006.01)
*A61B 19/00* (2006.01)

(52) U.S. Cl. .............. 604/411; 604/905; 604/533; 604/33; 251/149.9; 137/614

(58) Field of Classification Search ............ 604/403, 604/411, 413, 905, 533, 507, 537–539, 317, 604/513, 288.03, 33; 251/149.9, 148; 137/614, 137/614.04, 614.03, 614.06
See application file for complete search history.

(56) References Cited

U.S. PATENT DOCUMENTS

| 2,823,887 | A | * | 2/1958 | Osinski ............... 251/148 |
| 4,089,506 | A | * | 5/1978 | Blake ................. 251/196 |
| 4,187,846 | A |   | 2/1980 | Lolachi et al. |
| 4,306,705 | A |   | 12/1981 | Svensson |

(Continued)

FOREIGN PATENT DOCUMENTS

DE           10039196           2/2002

(Continued)

OTHER PUBLICATIONS

Copy of International Search Report dated Nov. 14, 2003.

*Primary Examiner*—Tatyana Zalukaeva
*Assistant Examiner*—Leslie R Deak
(74) *Attorney, Agent, or Firm*—Millipore Corporation

(57) ABSTRACT

A sterile to sterile connection device comprising a connector and one or more coupling devices. The connector has body portion which has two openings sealed from the environment so as to form a sterile environment within the connector. At least one of the openings being sealed from the environment by a sterile barrier plug. The connector also has a port capable movement within the body of the connector to at least an open and a closed position. The coupling device is formed of a body having two openings and a stem having a bore through at least a portion of the stem. The stem is contained within the body and capable of moving at least linearly through the body between a first and second stem position. One of the openings of the stem is sealed from the environment by a sterile barrier plug and the other is sealed to a presterilized component. The coupling device opening containing the sterile barrier plug is attached to either the inlet or outlet of the connector.

11 Claims, 14 Drawing Sheets

U.S. PATENT DOCUMENTS

| | | | |
|---|---|---|---|
| 4,456,026 A * | 6/1984 | Kantor | 137/315.29 |
| 4,534,758 A * | 8/1985 | Akers et al. | 604/85 |
| 4,705,073 A * | 11/1987 | Beck | 137/625.25 |
| 4,838,877 A | 6/1989 | Massau | |
| 5,360,413 A | 11/1994 | Leason et al. | |
| 6,341,802 B1 | 1/2002 | Matkovich | |

FOREIGN PATENT DOCUMENTS

| | | |
|---|---|---|
| EP | 0639389 | 2/1995 |
| EP | 0684050 | 11/1995 |
| GB | 2327369 | 1/1999 |
| WO | WO 98/45188 | 10/1998 |

* cited by examiner

STERILE CONNECTOR

The present invention relates to a connector for establishing a sterile to sterile connection. More particularly, it relates to a connector for establishing a disposable sterile to sterile connector for use in the medical, pharmaceutical and biopharmaceutical industry.

BACKGROUND OF THE INVENTION

In the pharmaceutical, biotechnology and even food, beverage and cosmetics industries, it is often desired to provide a processing system that is capable of handling fluids in a sterile manner. This is designed to prevent unwanted, often dangerous organisms, such as bacteria as well as environmental contaminants, such as dust, dirt and the like from entering into the process stream and/or end product. It would be desirable to have a completely sealed system but this is not always possible with the processes that take place in production.

There is a need for the introduction or removal of materials from the process stream in order to add components of the product, such as media or buffers to a bioreactor; withdraw samples from the process stream to check for microbial contamination, quality control, process control, etc; and to fill the product into its final container such as vials, syringes, sealed boxes, bottles and the like.

Typically, the systems have been made of stainless steel and the system is exposed to live steam before use and then cleaned with chemicals such as caustic solutions after use to ensure that all contaminants are removed.

Steaming is the most effective means of sterilization. The use of steam in a set system is known as steaming in place or SIP. Saturated steam carries 200 times the BTU heat transfer capacity of heated air because of the latent heat released by the steam as it changes from vapor to liquid.

Several disadvantages exist with the use of steam. Any connections to or openings of the system made after the system has been SIP'd is an aseptic (but not sterile) connection or opening. This increases the risk of contamination of the entire system. One typically uses alcohol wipes or an open flame to clean the components to be connected, (e.g. connecting a sample collection bag to a system after SIP has occurred) and thus minimize the risk of contamination.

Also the high temperatures and pressure differentials of the steam make the selection of materials and components very difficult and limited and even then an accidental pressure differential at high temperatures can cause a non-steel component to fail.

Additionally, such systems that are reused need to undergo rigorous testing and validation to prove to the necessary authorities that the system is sterile before each use. The expense of validation as well as the cleaning regiment required is very high and very time consuming (typically taking 1 to 2 years for approval). In addition, some components are very difficult to adequately clean after use.

As an alternative to requiring a sterilization step with steam, some systems have advocated the use of alcohol wipes and other bactericides on the adjoining parts before assembly. While this may significantly reduce the presence of organisms, it does not eliminate them and at best this provides an aseptic connection.

U.S. Pat. No. 6,341,802 teaches the use of peelable membranes formed on the outer surfaces of two mating components. The membranes are exposed to the environment. Layers beneath of two outer membranes are sterile. The membranes are mated and the two devices attached and the membranes are then pulled out of the union between the two components. A piercable probe extends through the sterile barriers that face each other to form an environmentally tight seal. This approach is cumbersome and there is still some risk of contamination in the removal of the outer membranes. Also the use of piercing device creates the generation of particles that are unacceptable as well as the potential for tearing the seals between the two components that might add more contaminants to the system or clog the openings. Lastly, the device is limited in size making its use at large volumes or flows impracticable.

In a further improvement, a connector or valve can be formed that has a nonsterile closed face and a presterilized (typically with gamma radiation) downstream component(s) (such as a tubing and bag assembly). The face of the device is then attached to the desired equipment such as a port of a bioreactor or storage tank, or attached to a pipe fitting by a Tri-Clover® or Ladish fitting. The face along with the rest of the system upstream of the face is then steam sterilized in place (SIP). When the face is open after steaming, a sterile connection is achieved.

What is still desired is a simple, reliable sterile connection device that allows for a sterile to sterile connection without the need for steam or other cumbersome procedures.

SUMMARY OF THE INVENTION

The present invention is a connection device comprising a connector and one or more coupling devices. The connector has body portion that has two openings, each opening being sealed from the environment so as to form a sterile environment within the connector. At least one of the openings being sealed from the environment by a sterile barrier plug. The connector also has a port capable movement within the body of the connector to at least two positions. The at least one coupling device is formed of a body having two openings and a stem having a bore through at least a portion of the stem. The stem is contained within the body and capable of moving at least linearly through the body between a first and second stem position. One of the openings of the stem is sealed from the environment by a sterile barrier plug and the other is sealed to a presterilized component. The coupling device opening containing the sterile barrier plug is attached to either the inlet or outlet of the connector.

The present invention also relates to a process for establishing a sterile connection between two or more components. The process uses a connection system comprising a connector and one or more coupling devices. The process is to attach the opening of the stem that is attached to the connector is sealed from the environment by a sterile barrier plug to the opening of the connector containing the plug. The port is in the first, closed position and the stem is in its first position. The port and stem are advanced to their second positions and the plugs of the stem and the port are both moved to within the port. The port is then advanced to its third open position, moving the plugs out of the way and establishing a fluid communication between the port and the rest of the connector. The stem is then extended to its third position making a positive peripheral liquid tight seal with the port and establishing fluid communication between the coupling device and the connector.

The present invention also relates to a sterile to sterile connection system formed of a connector with a port capable of two or more positions and a coupling device. All openings into both elements are sealed from the environment and contamination. The devices are connected and rotated respective to each other to align the port in a manner so that it removes any sterile barrier plugs and establishes a sterile fluid communication throughout the device.

In another embodiment, the device consists of a connector having two portions an upper portion and a bottom portion depending downwardly from the top portion at a selected angle. The bottom portion contains a movable stem within its bore. The second element is coupling device containing a stem within its bore. The end of the stem that mates with the connector is sealed by a sterile plug. The end of the connector that seals with the coupling device also has a sterile plug. The stem of the coupling device is used to push both plugs into the top portion of the connector to a point beyond the opening between the top and bottom portions so as to establish fluid communication through the system.

In another embodiment, the device consists of a connector having two portions an upper portion and a bottom portion depending downwardly from the top portion at a selected angle. The bottom portion contains a movable stem within its bore. The second element is a coupling device containing a stem within its bore. The end of the stem that mates with the connector is a garage having its outer end sealed by a sterile plug. The garage contains two intersecting bores. The end of the connector that seals with the coupling device also has a sterile plug. The stem of the coupling device is used to push the garage and plug into the top portion of the connector to a point at which one of the bores of the garage aligns with the opening between the top and bottom portions so as to establish fluid communication through the system.

IN THE DRAWINGS

FIG. 1 shows a first embodiment of the present invention in exploded view.

FIGS. 2A–F show the process of assembling and connecting the device of FIG. 1.

Figure 3:
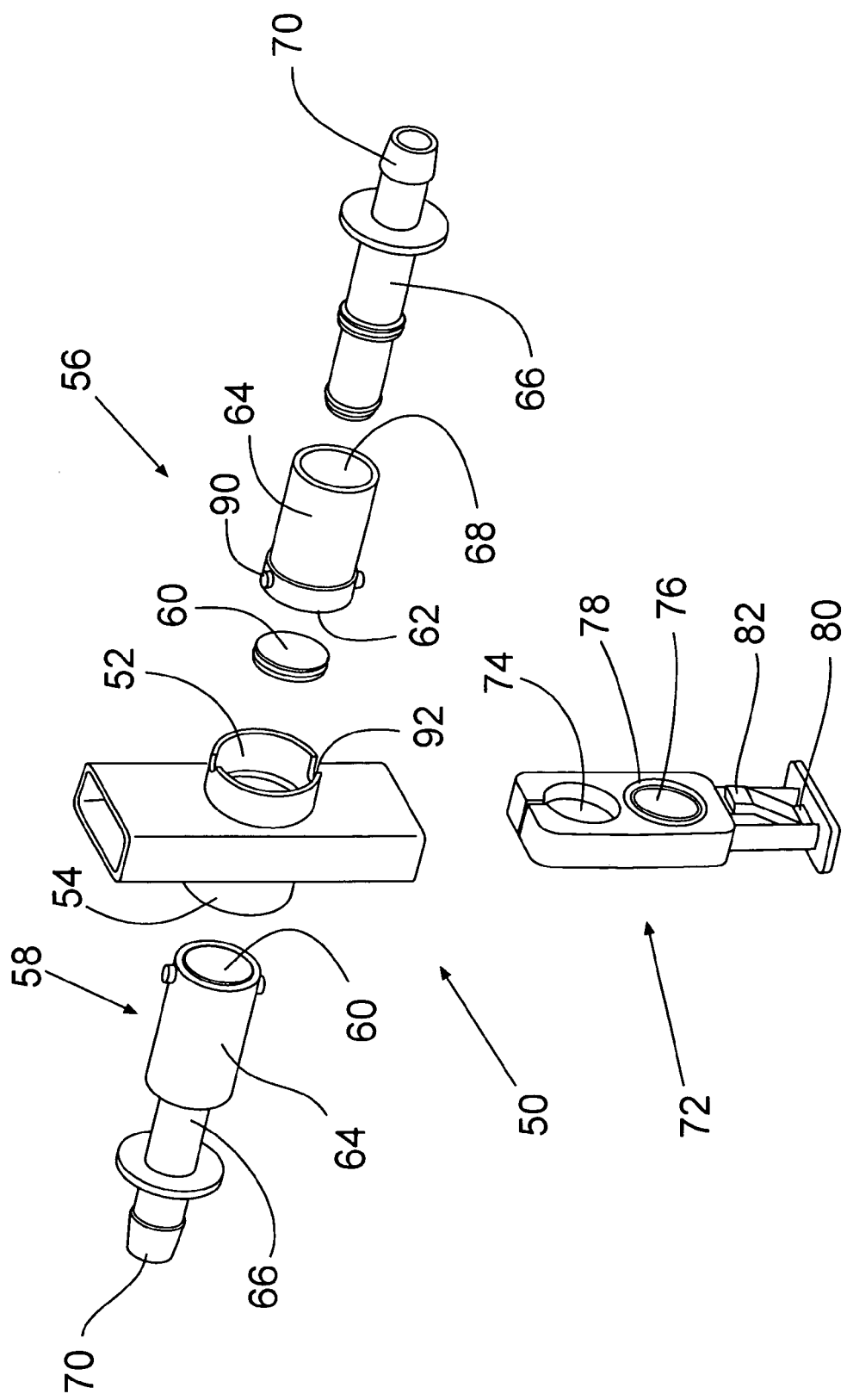
FIG. 3 shows a second embodiment of the present invention in exploded view.

FIGS. 5A–E show the process of assembling and connecting the device of FIG. 3.

Figure 6:
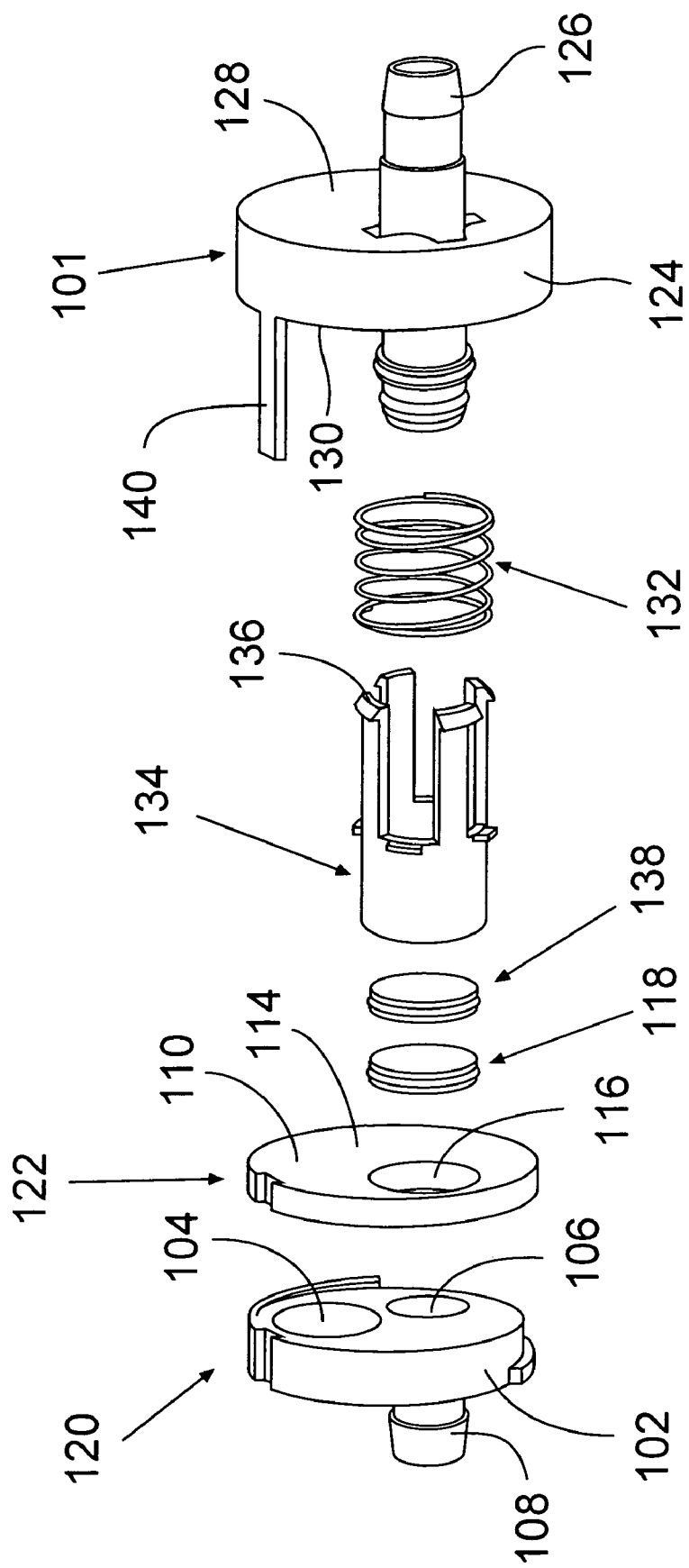

FIG. 6 shows a third embodiment of the present invention in exploded view.

FIGS. 7A–E show the process of assembling and connecting the device of FIG. 6.

Figure 8:
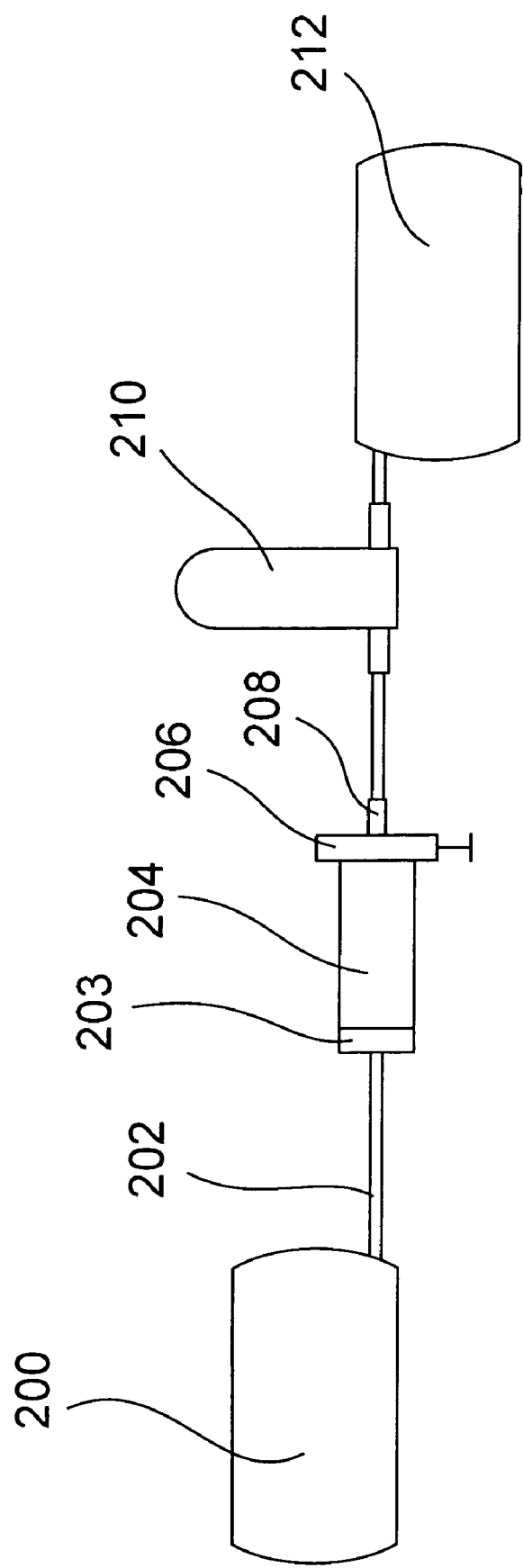

FIG. 8 shows a device of the present invention in a first contemplated use.

Figure 9:
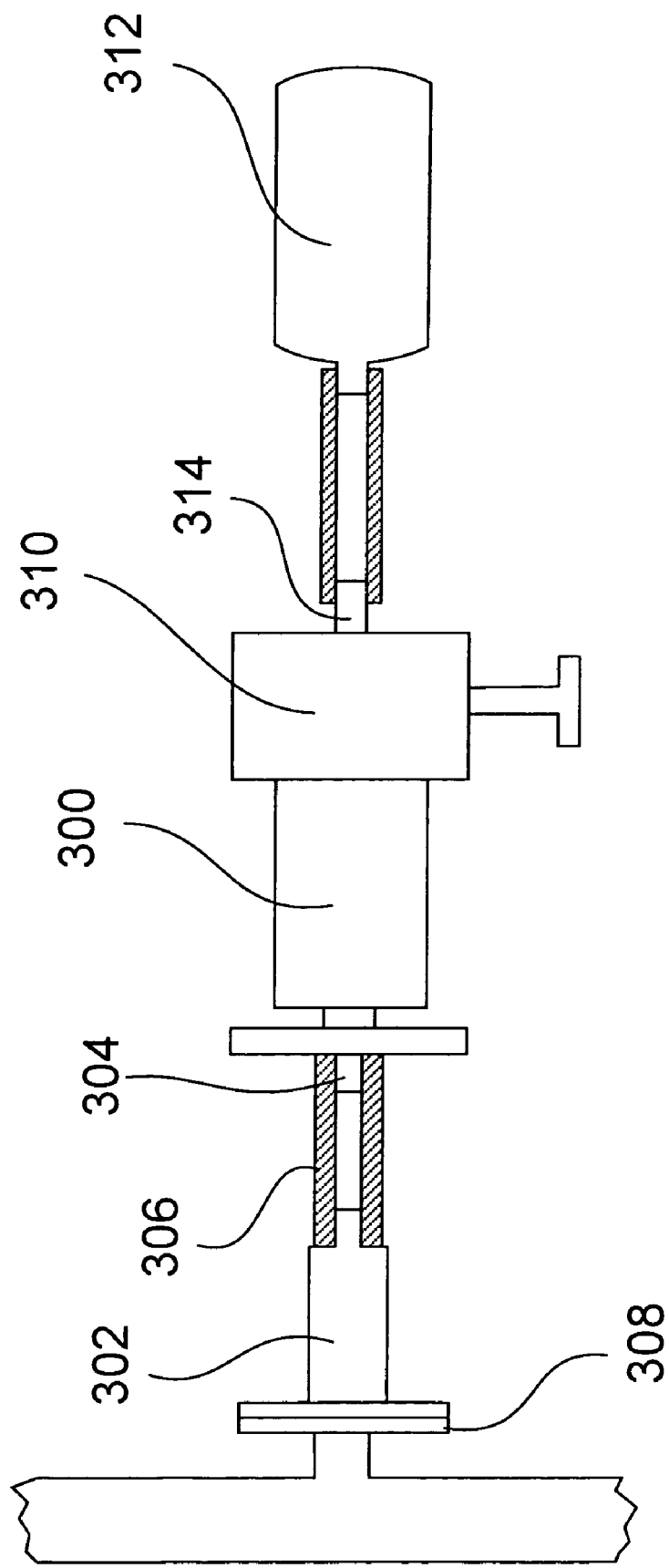

FIG. 9 shows a device of the present invention in a second contemplated use.

Figure 10:
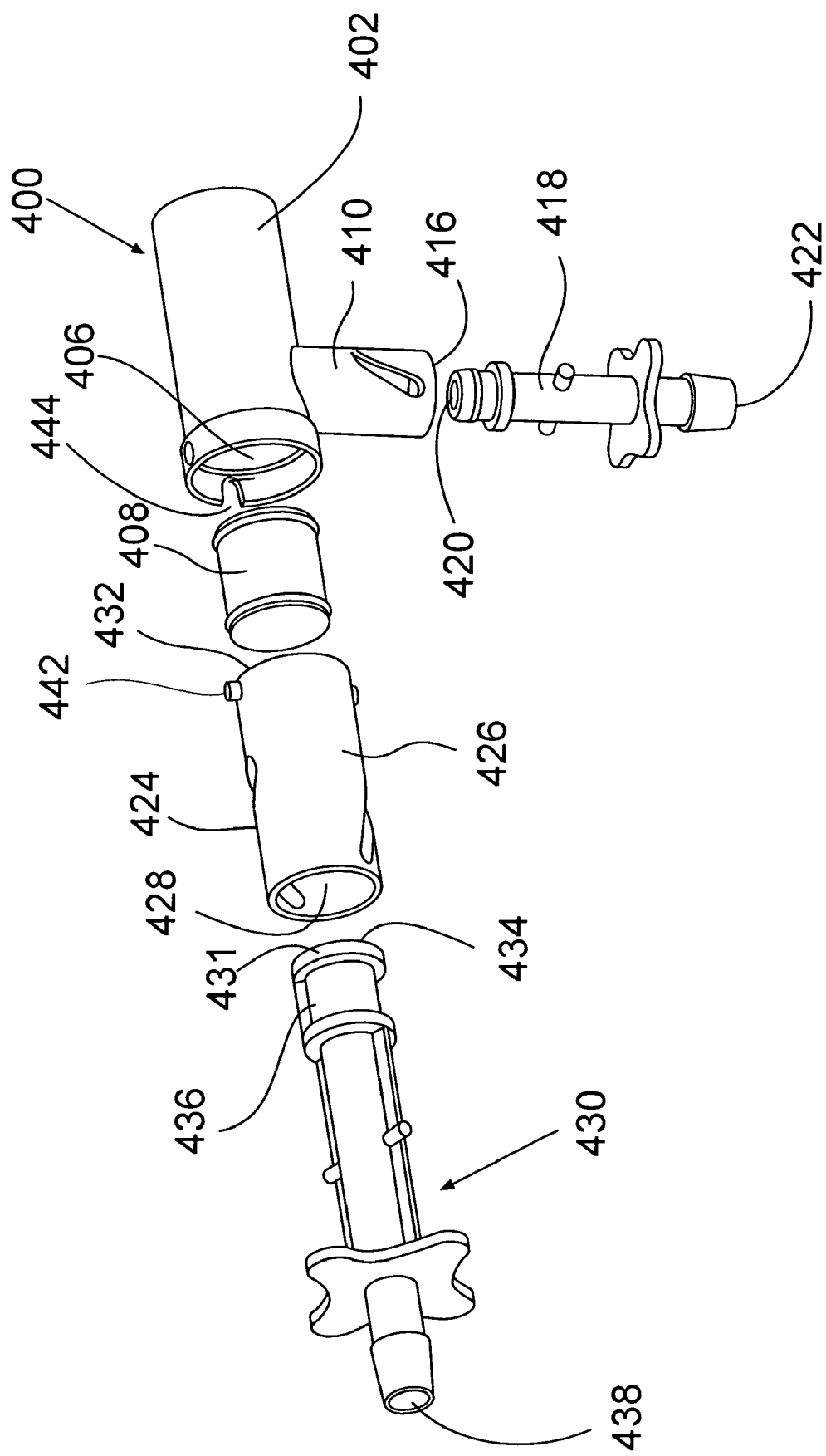

FIG. 10 shows a third embodiment of the present invention in exploded view.

Figure 11A:
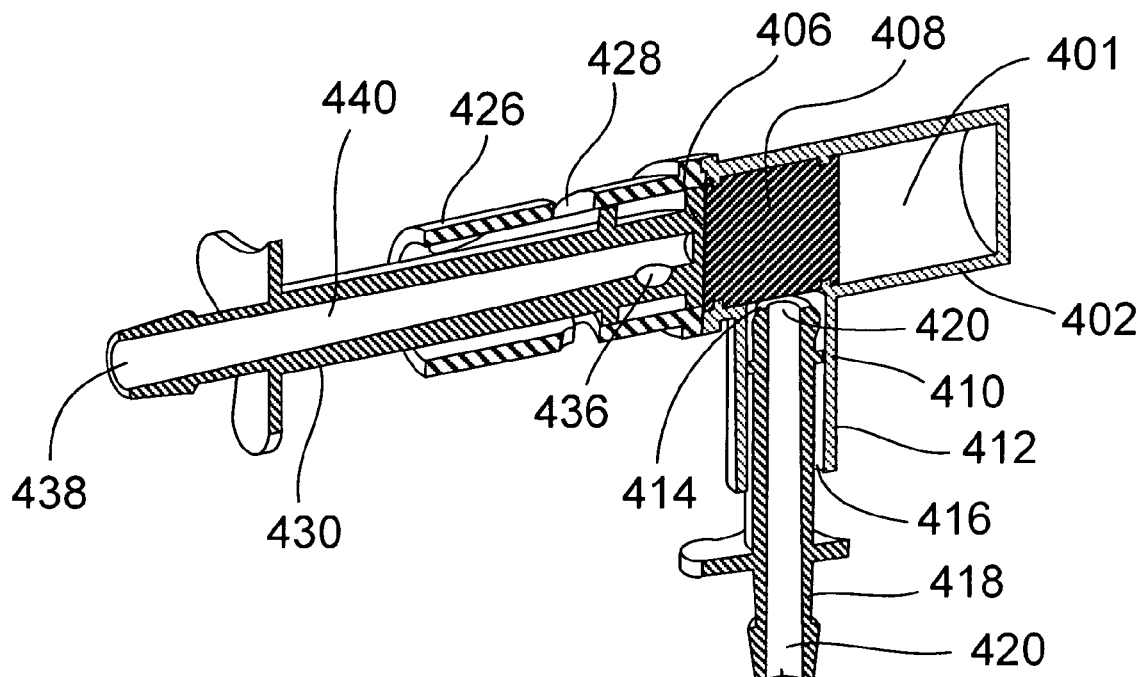
Figure 11B:
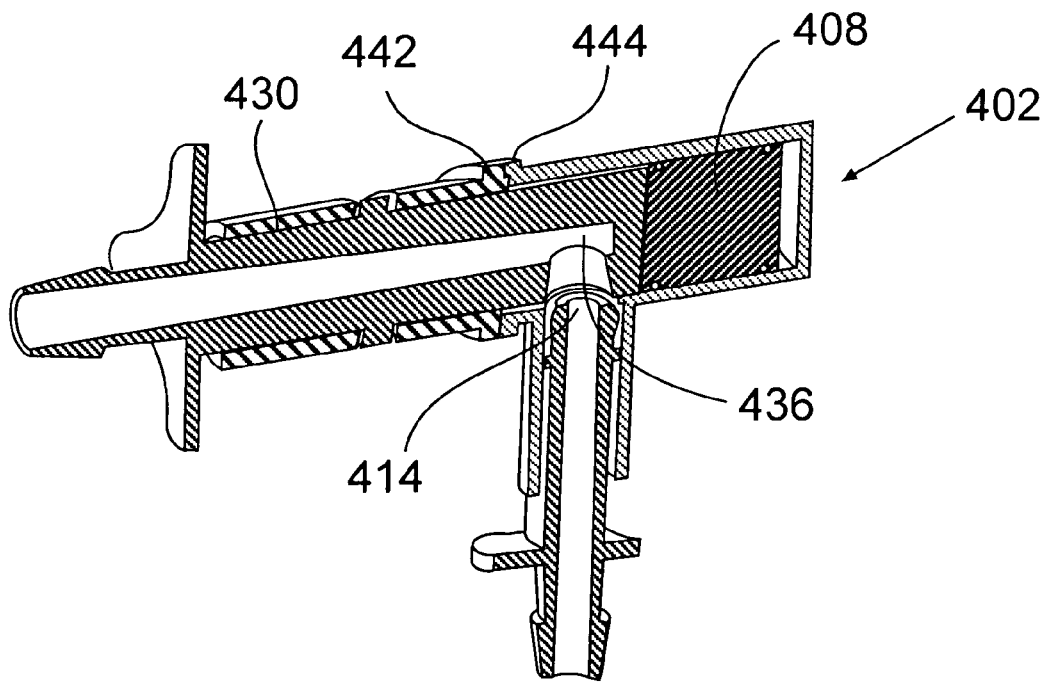
Figure 11C:
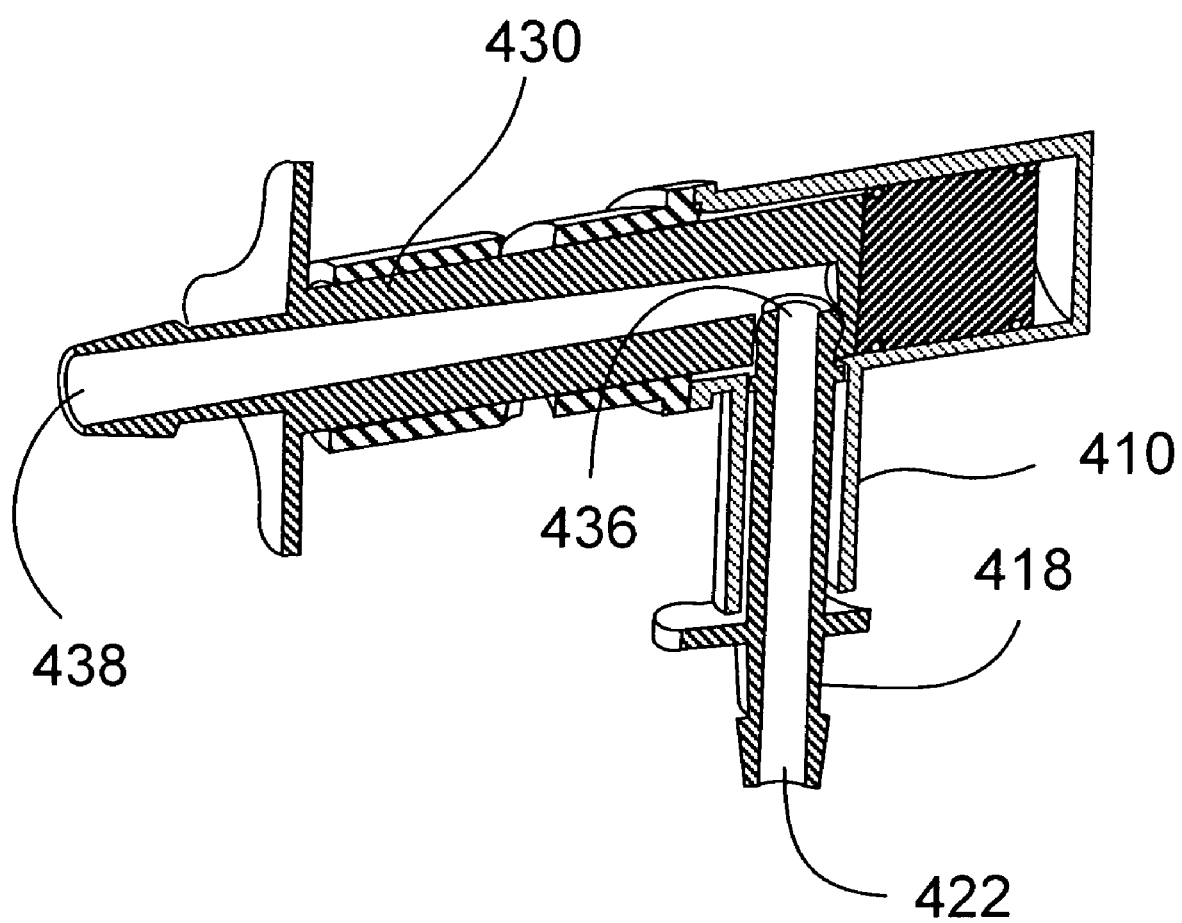

FIGS. 11A–C show the process of assembling and connecting the device of FIG. 10.

Figure 12:
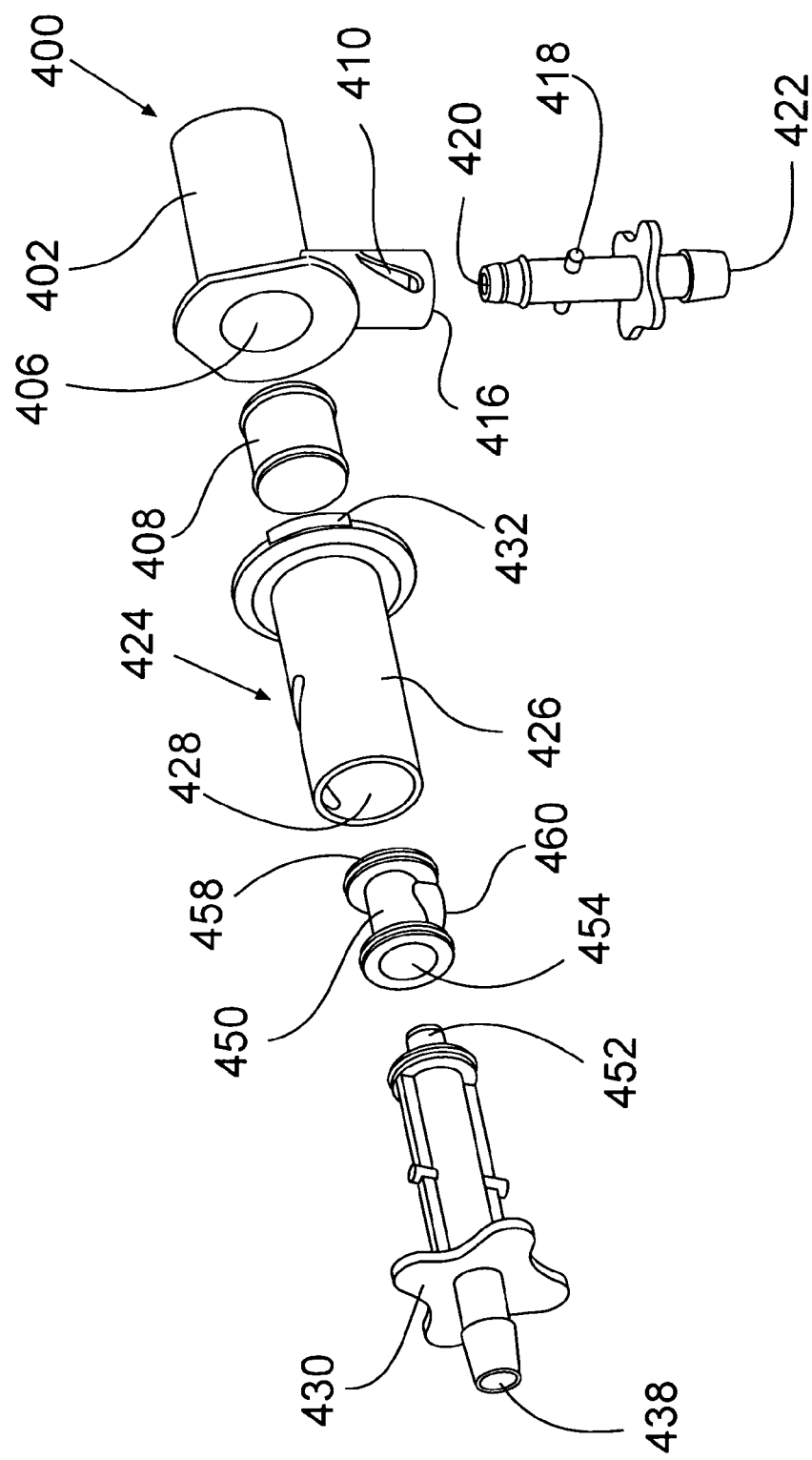

FIG. 12 shows a fourth embodiment of the present invention in exploded view.

FIGS. 13A–D show the process of assembling the device of FIG. 12.

DETAILED DESCRIPTION OF THE INVENTION

Figure 1:
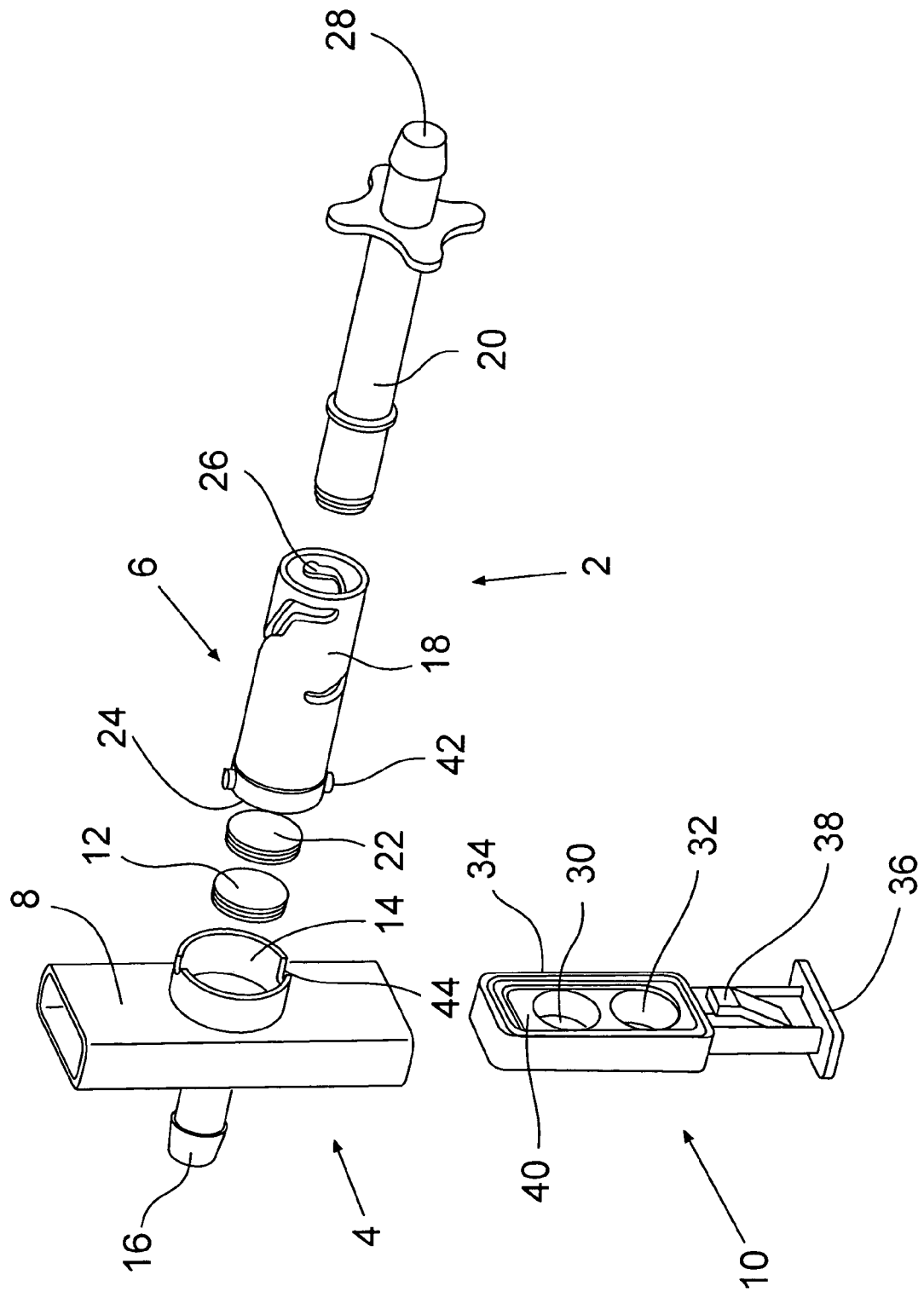

FIG. 1 shows a first embodiment of the present invention. In this embodiment one sees the two basic components a device 2 of the present invention, the connector 4 and the coupling device 6. The connector is formed of three components, a body 8, a movable port 10 and a sterile barrier plug 12. The connector in this embodiment also has a first opening 14 that is sealed by the sterile barrier plug 12 when the device is in a closed position and a second opening 16, in this embodiment in the form of a barbed connector that is connected to another sterile component (not shown).

The other basic component of the device 2 is the coupling device 6. It is formed of a body 18 a movable stem 20 contained within a portion of the body 18 and a sterile barrier plug 22 located in a first opening 24 of the coupling device. The stem 20 is contained within the second opening 26 of the coupling body. The stem 20 also has an opening 28 extending outwardly from the second opening 26 of the coupling body 18. It again in this embodiment is in the form of a barbed connector that is attached to a sterile component (not shown).

The port 10 is in the form of a slide that fits within the body 8 of the connector 4. The port has the ability of being in one of three positions, closed, partially open and fully open. It also contains a first opening 30 and a second opening 32. To ensure sterility of the port 10 and the device 2 it also contains a perimeter seal 34 around the two openings 30, 32. The port as shown also has an actuating device 36, in this embodiment in the form of a handle. The handle 36 in this embodiment also contains a latch 38 that is used to lock the port 10 in its open position when so actuated.

Figure 2C:
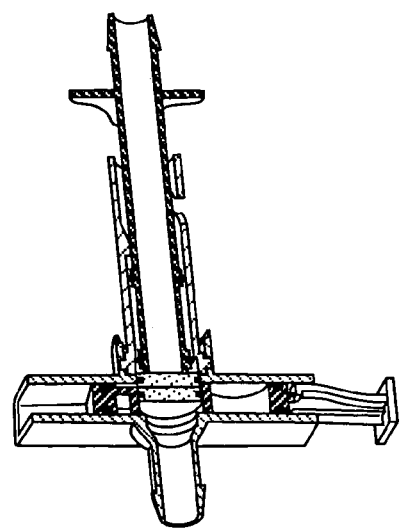
Figure 2B:
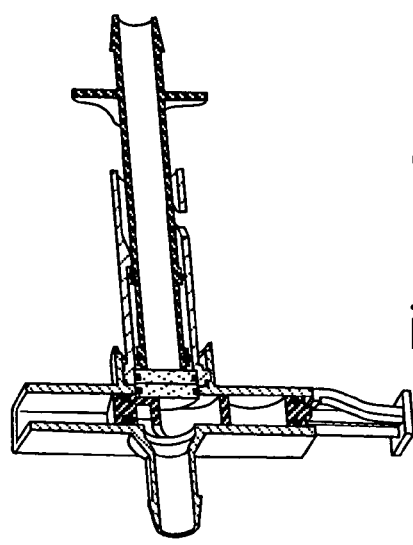
Figure 2A:
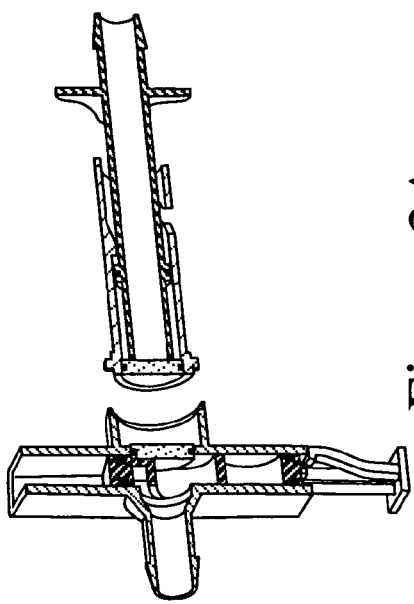

FIGS. 2A–F show the assembly of the device 2 of FIG. 1. In FIG. 2A, the device 2 is shown in the sterile closed position. The connector 4 has its first opening 14 sealed by the sterile barrier plug 12. Its second opening 16 is connected to a sterile component (not shown). The port is in its closed position with a portion of the port 40 supporting the sterile plug 12 and maintaining it in its position within the connector 4. (See also FIG. 1 for another view of the portion 40) Also shown in FIG. 2A is the coupling device 6 with the sterile plug 22 sealing the first opening 24 of the coupling device 6 from the environment. The stem 20 is contained in the body 18 of the coupling device 6.

In FIG. 2B, the coupling device is being attached to the connector by mating the first ends of the connector and the coupling device together. This may be a friction fit. Alternatively there may be a more secure fitting between the components to ensure that they stay together and remain sterile. The use of mating threads, snap connections, movable pawls and the like may be used to make such a secure connection. As shown in FIGS. 1 and 2A, the coupling device uses a series of nubs 42 which lock into corresponding grooves 44 (of FIG. 1) to make this connection.

In FIG. 2C, the port 10 is moved from its closed position to its partially open position by moving the port 10 linearly into the body 8 of the connector 4 such that its first opening 30 is now in line with sterile plugs 12 and 22 and its portion 40 is no longer supporting the sterile plug 12 within the body 8 and the connector 4. Optionally, the port 10 and connector body 8 may contain a detent or other locking mechanism (not shown) that ensures that the port 10 cannot inadvertently slip back into the closed position.

Figure 2F:
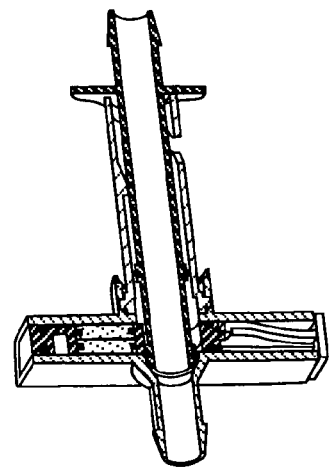
Figure 2E:
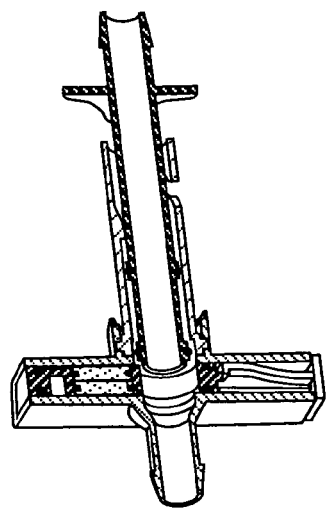
Figure 2D:
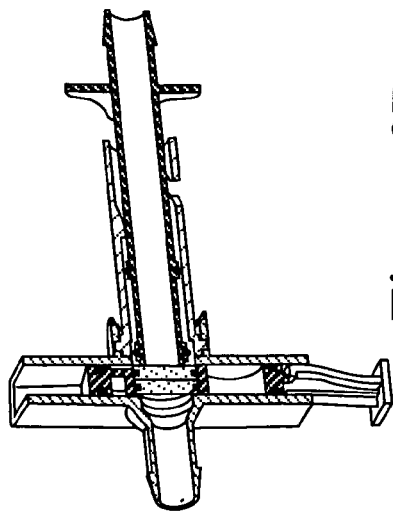

In FIG. 2D, the stem 20 is moved inward toward the connector 4 moving the sterile plugs 12 and 22 into the first opening 30 of the port 10. The stem 20 may move linearly or both linearly and rotationally in this procedure.

In FIG. 2E, the port 10 is then moved to its open position aligning its second opening 32 with the second opening of the connector body and the first opening 24 of the coupling device 6. This establishes a fluid communication between the second opening of the connector and the second opening of the coupling device.

In FIG. 2F, the stem is advanced through the second opening 32 and forms a liquid tight and hermetic seal with a portion of the second opening 16 of the connector 4. A fluid, be it gas or liquid can now be flowed through the device 2 in a sterile manner.

FIG. 3 shows another embodiment of the present invention. In this embodiment, the connector 50 has a first and second opening 52 and 54 respectively it has two coupling devices 56 and 58. These coupling devices each contain a sterile plug 60 in the first opening 62 of the coupling body 64, a stem 66 within that body 64 and extending outwardly of the second opening 68 of the body 64. Each stem portion that extends out from the second opening of the body has a second opening 70 that is connected to a presterilized component (not shown).

The port 72 is in the form of a slide that fits within the body of the connector 50. The port 72 has the ability of being in one of at least two positions, closed and fully open. It also contains a first opening 74 and a second opening 76. To ensure sterility of the port 10 and the device 2 it also contains a perimeter seal 78 around opening 76. The port 72 as shown also has an actuating device 80, in this embodiment in the form of a handle. The handle 80 in this embodiment also contains a latch 82 that is used to lock the port 72 in its open position when so actuated.

Figure 4:
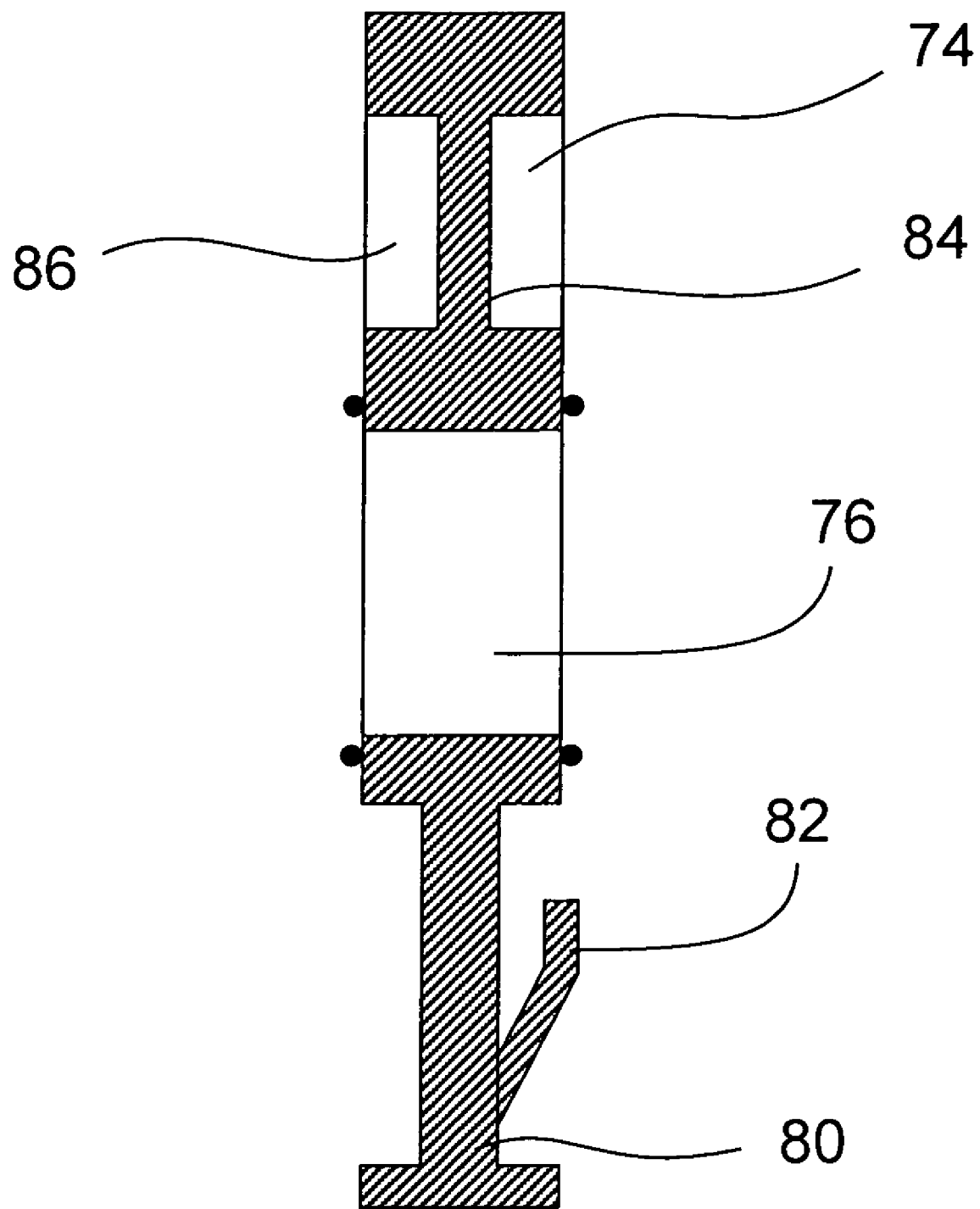
FIG. 4 shows a cross sectional view of the port of FIG. 3.

Unlike the port 10 of FIG. 1, the first opening 74 of the port 72 in this embodiment, as shown more clearly in FIG. 4, is actually formed of two recesses 84, 86, one each facing the respective first and second openings of the connector 50 with a wall 88 between the two recesses 84, 86. The connector in this embodiment has no sterile barrier plugs.

To assemble and use the embodiment of FIG. 3, one follows the steps of FIGS. 5A–E.

Figure 5B:
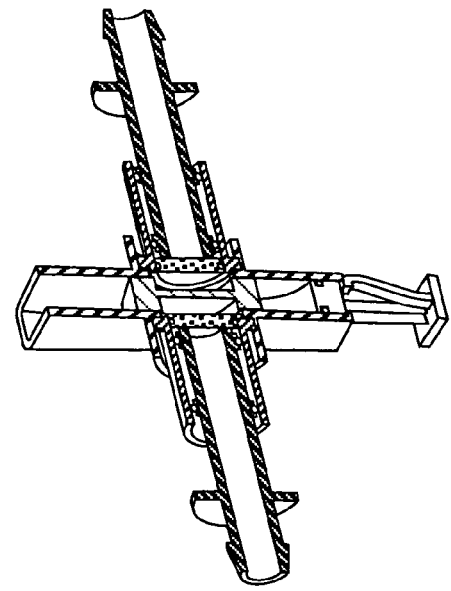
Figure 5E:
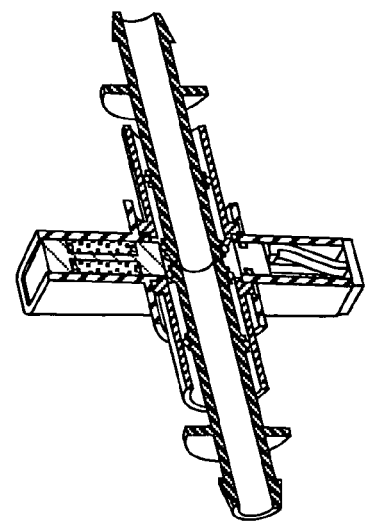
Figure 5A:
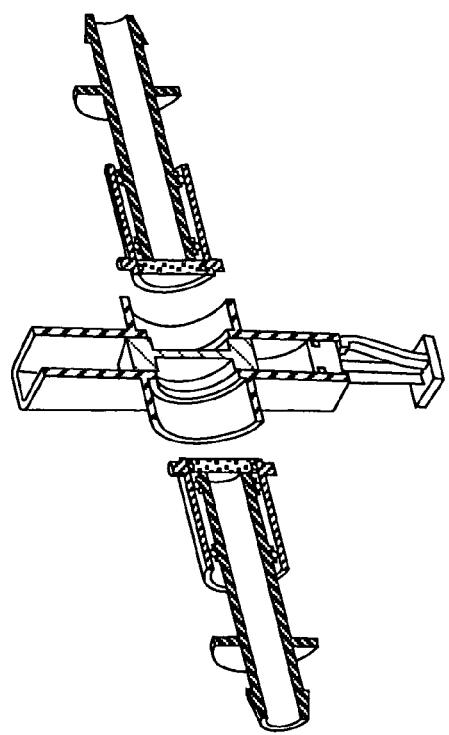

In FIG. 5A, the connector 50 and two coupling devices 56 are shown in their closed unassembled state. Coupling devices have already been connected to their other component (not shown) by second opening 70 the stems 66 and then sterilized such as by gamma irradiation, gases such as ethylene oxide, steam or the like.

In FIG. 5B, the coupling devices 56 are attached to the connector by mating the first ends the coupling devices to the first and second openings of the connector respectively. This may be a friction fit. Alternatively there may be a more secure fitting between the components to ensure that they stay together and remain sterile. The use of mating threads, snap connections, movable pawls and the like may be used to make such a secure connection. As shown in FIGS. 3 and 5A, the coupling device uses a series of nubs 90 which lock into corresponding grooves 92 (of FIG. 3) to make this connection. Optionally, the connector and coupling devices 56 are locked together in a manner that prevents them from becoming inadvertently undone. In one preferred embodiment, the locking of the components together is irreversible to ensure single usage.

Figure 5D:
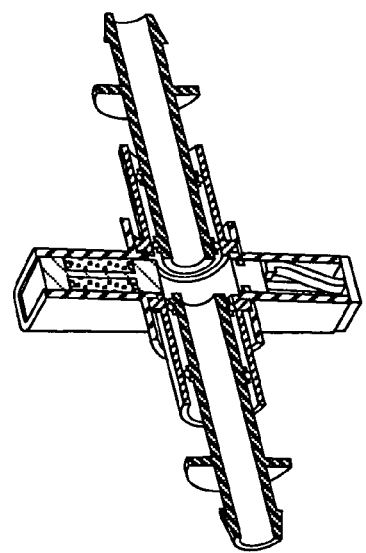
Figure 5C:
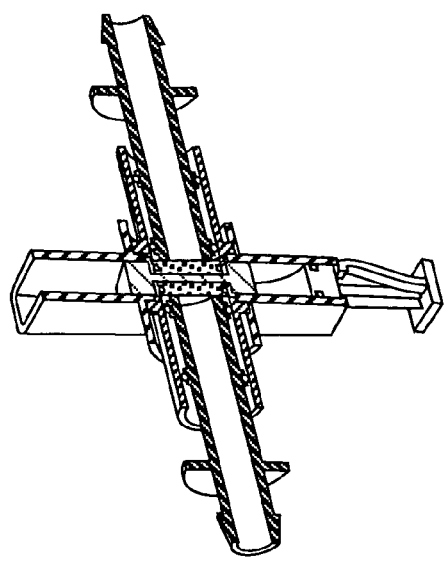

In FIG. 5C, each stem is moved toward the connector so as to move the sterile plugs 60 of each coupling device into the first opening 74 of the port 72.

In FIG. 5D, the port is moved to its second position, creating a fluid pathway and fluid communication between the two coupling devices.

In FIG. 5E, the stems are moved into a fully open position, sealing against each other.

FIG. 6 shows another embodiment of the present invention. In this embodiment, one uses both linear as well as rotational movements of different elements to create the sterile pathway. The connector 100 is formed of a port 102 that has a first opening 104 and a second 106. This second opening 106 extends through the body of the port and creates the second opening 108 of the connector 100 (in this embodiment in the form of barbed connector). The connector also has a second body portion 110 that has a first and second major face 112 and 114 respectively. The second portion 110 is connected to the port by its first face 112. The second portion 110 contains a first opening 116 that extends through the depth of the second body from the first face 112 to the second face 114. A sterile plug 118 is contained within the opening 116 in the closed position. Optionally, at least the second portion 110 and preferably both the port 102 and the second portion 110 contain a keyway 120 and 122 as shown in FIG. 6. The two portions of the connector may be held together by a variety of devices any of which are suitable so long as they allow for the easy rotation of the two elements relative to each other. For example, one portion can contain an undercut around its outer peripheral edge and the other portion has a mating rim to fit that undercut and rotate within it. Another device is a simple center pivot that connects the two portions together by glue, mechanical retention and the like.

The coupling device 101 is comprised of a body 124 that has a second opening 126 on one face 128 of the body 124 and a first opening 128 in fluid communication with the second opening 124 on a second face 130 of the body 124. Surrounding the first opening 128 is a compression spring 132 and a coupling drum 134. The drum 134 is attached to the second face 130 of the body 124 by a series of detents 136 that fit into a series of retainers (not shown) on second face 130. The first opening is sealed off from the environment by a sterile plug 138 located at the end of the drum 134 furthest from the second face 130 of the body 124. Also shown on the body 124 is a key 140.

Figure 7A:
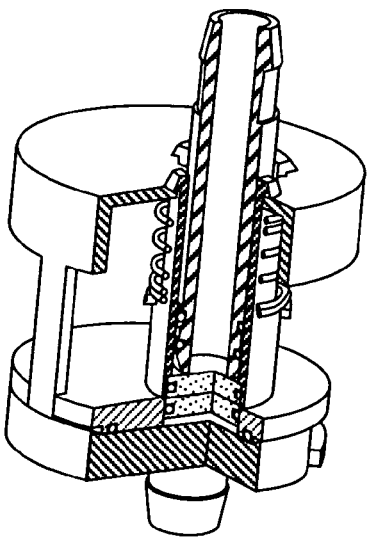

FIG. 7A shows the two components 101 and 102 in the first step of assembly. Both components are sealed off from the environment and each other by the sterile plugs 118 and 138. Drum 134 is placed against the plugged opening 116 such that both plugs 118 and 138 meet and make contact with each other. Also as shown key 140 fits into the keyway 122.

Figure 7B:
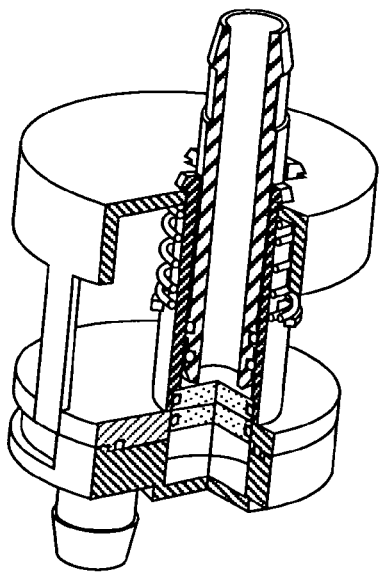

In FIG. 7B, the second portion 110 and coupling device 101 are rotated to align the opening 116 with the opening 104 of the port 102. Drum 134 is pushed into the opening 116 by the spring 132 and is essentially coterminous with opening 116 where it meets the port.

Figure 7C:
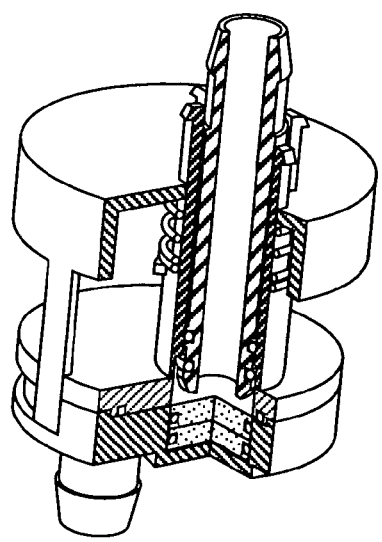

Plugs 118 and 138 are moved into opening 104 by the same action as is shown in FIG. 7C.

Figure 7D:
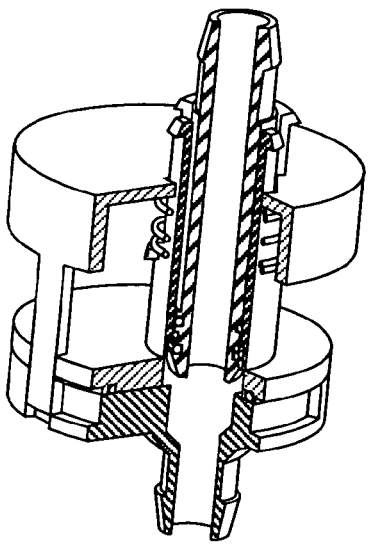

In FIG. 7D, the port and the second portion/coupling device combination are rotated relative each other to align opening 106 with drum 134. Key 140 also now aligns with keyways 122 and 120.

Figure 7E:
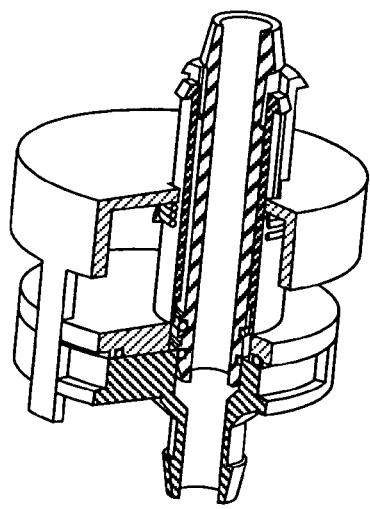

In FIG. 7E, the assembly is moved linearly toward each other to form a fluid pathway between opening 108 and opening 126 through the coupling device 101 and the connector 100. As described above various locking mechanisms can be used to hold the components in place and maintain the sterile connection that has been established.

The device may be formed of metal or plastic. Preferably it is formed a plastic material and may be formed by machining the respective assemblies and then applying the necessary seals and the like, or preferably by molding the respective components separately and assembling them together with the necessary seals and other components.

The device may be made of any material capable of some type of sterilization, be it steam, pressurized steam, chemical or radiation. Preferably, the entire device is made of the same material and is capable of withstanding the selected sterilizing conditions. Suitable materials for this device include but are not limited to polyolefins such as polyethylene or polypropylene, carbonates, styrenes, EVA copolymers, polyvinyl chlorides, PVDF, PTFE, thermoplastic perfluoropolymers such as PFA and MFA, PEI (polyetherimide), PEEK, PEK, polysulphones, polyarlysulphones, polyalkoxysulphones, polyethersulphones, polyphenyleneoxide, polyphenylenesulphide and blends thereof as well as thermosets such as epoxies, urethanes, cyanurates and the like.

The seals which may be in the form of O-rings, gaskets and the like of the present invention can be made of a variety of materials typically used for making resilient seals. These materials include but are not limited to natural rubber, synthetic rubbers, such as silicone rubbers, including room temperature vulcanizable silicone rubbers, catalyzed (such as by platinum catalysts) silicone rubbers and the like, thermoplastic elastomers such as SANTOPRENE® elastomers, polyolefins such as polyethylene or polypropylene, especially those containing gas bubbles introduced either by a blowing agent or entrained gas such as carbon dioxide, PTFE resin, thermoplastic perfluoropolymer resins such as PFA and MFA resins available from Ausimont, USA of Thorofare, N.J. and E.I. DuPont de Nemours of Wilmington, Del., urethanes, especially closed cell foam urethanes, KYNAR® PVDF resin, VITON® elastomer, EPDM rubber, KALREZ resin and blends of the above. Suitable materials for molded in place seals can be curable rubbers, such as room temperature vulcanizable silicone rubbers, thermoplastic elastomers such as SANTOPRENE® elastomers, polyolefins such as polyethylene or polypropylene, especially those containing gas bubbles introduced either by a blowing agent or entrained gas such as carbon dioxide and elastomeric fluoropolymers Other materials used in the devices should also be FDA grade components such as FDA grade rubbers and silicones, PTFE resins and the like.

This device may be used in any situation requiring a sterile to sterile connection. For example in the medical filed it may be used to create sterile connections between a blood, serum or buffer solution bag or a dialysis bag and a patient. In pharmaceutical manufacturing, especially disposable manufacturing, it may be used to create sterile connections between different components of the process such as connecting a bioreactor to a filter and then to a storage bag. This is shown in FIG. 8 where a bioreactor bag 200 is connected to an opening 202 of the stem 203 of a coupling device 204. The connector 206 has its second opening 208 attached to downstream components such as capsule 210 containing a filter such as an OPTICAP® filter available from Millipore Corporation of Bedford, Mass. It 210 in turn is connected to a collection bag 212. As shown coupling device 204 and connector 206 were provided in a sterile condition connected to their respective upstream and downstream components as shown and then assembled as described above in relation to FIGS. 2A-F to establish fluid communication between all of the components.

This device may also be used in combination with a connector that is used to connect to an unsterilized component that then sterilized in place by steam. FIG. 9 shows such a use. The coupling device 300 has a steamable sterile connector 302 attached to its second opening 304 via tubing 306. The steamable connector has a closed face that is capable of being steam sterilized when attached to a system such as the pipe shown in this Figure. Such a steam sterilizable connector is available from Millipore Corporation and is described in co-pending application U.S. Ser. No. 60/375,747 filed Apr. 26, 2002. This assembly is provided in a sterilized condition such as gamma irradiating the closed assembly. The steamable connector 302 is attached to a component such as the pipe connection 308 shown and is then its face is steam sterilized in place. Coupling device is then attached to connector 310 that is connected to a collection bag 312 at its second opening 314. Connector 310 and bag 312 have also been previously sterilized before being connected to the coupling device 300. The bag can be used as a collection, sample or a waste bag in a process stream.

FIG. 10 shows another embodiment of the present invention. In this embodiment, the connector 400 is in the form of a "T". The top portion 402 has a bore (404, See FIG. 11A) with an open end 406 in which a sterile barrier plug 408 resides to seal the top portion from the environment and contamination. The bottom portion 410 depends downwardly from the top portion 402. While shown as being substantially perpendicular to the major axis of the top portion 402, the union of the bottom portion 410 may be less than or greater than perpendicular if desired. The bottom portion 410 contains a bore (412 of FIG. 11A) having two open ends, one (414 of FIG. 11A) ending in fluid communication with the bore 404 of the top portion 402 and the other 416 being at the other end of the bottom portion away from the top portion 402. This opening 416 is sealed by a movable stem 418 that has a bore 420 (FIG. 11A) extending through it. The first end of the bore 420 connects with the bore 404 of the connector 400. The other end 422 is connected to a sterile element such as a collection bag (not shown) connected to the opening (which in this embodiment is in the form of a barbed nipple).

The coupling device 424 is formed of body 426 having a throughbore 428. A stem 430 is contained within the throughbore 428. A first end 431 of the stem 430 has a sterile barrier plug 434 mounted to it so that it forms a sterile seal at the first end 432 of the coupling device 424. At a point inward of the plug 434 is a first opening 436 (see FIG. 11A) of the stem 430. A second opening 438 of the stem 430 is at the end of the stem 430 opposite that of the first end 432 of the coupling device 424 with a bore 440 (FIG. 11A) running through the stem 430 from its first opening 436 to its second opening 438. Coupling device 424 also has one or more locking lugs 442 on its first end 432 that mate with one or more locking grooves 444 on the top portion 402 of the connector 400.

FIGS. 11A–C show how to assemble and use the embodiment of FIG. 10. As shown the connector and coupling device are provided in closed sterile conditions. The first end of the coupling device 424 is attached to the end of the top portion 402 of the connector 400 sealed by the plug 408. In this embodiment, one or more lugs 442 are mated with one or more grooves 444 to make the connection. Other means such as matable threads, snap fit connections or clamps could be used instead if desired.

FIG. 11B shows the movement of the stem 430 into the top portion 402 of the connector 400. This forces the plug 408 along the bore 404 of the top portion 402 to a position beyond that of the opening 414 of the connector 402 and aligns the first opening 436 of the stem 430 of the coupling device 424 with the opening 414.

In FIG. 11C the stem 418 of the bottom portion 410 of the connector 400 is advanced into the first opening 436 of the stem 430 to complete the sterile connection and establish a fluid communication between the second opening 438 of the coupling device 424 and the second opening 422 of the bottom portion 410 of the connector 400.

FIG. 12 shows a modification of the embodiment of FIG. 10. In this embodiment like elements corresponding to those of FIG. 10 use the same reference number. In lieu of the stem 430 having the sterile plug 434 mounted on its end, one uses a garage 450 which mates with the end of the stem 452. The bore 440 of the stem 430 has its first opening 436 inward of its end 452 and in this embodiment it is covered by the surface of the garage 450 to which the stem 430 mates when in the closed position. In this way the sterility of the stem bore 440 and opening 436 is doubly maintained. The garage 450 has a first bore 454 that mates with the end 452 of the stem 430. The second end 456 of the first bore is closed. It also has a sterile plug 458 mounted to the outer surface of its second end 456. A second bore 460 at an angle (preferably perpendicular, although other angles from 22.5 degrees to 157.5 degrees can be used) to the first bore 454 is also formed in the garage 450 and is in fluid communication with the first bore 454.

Figure 13A:
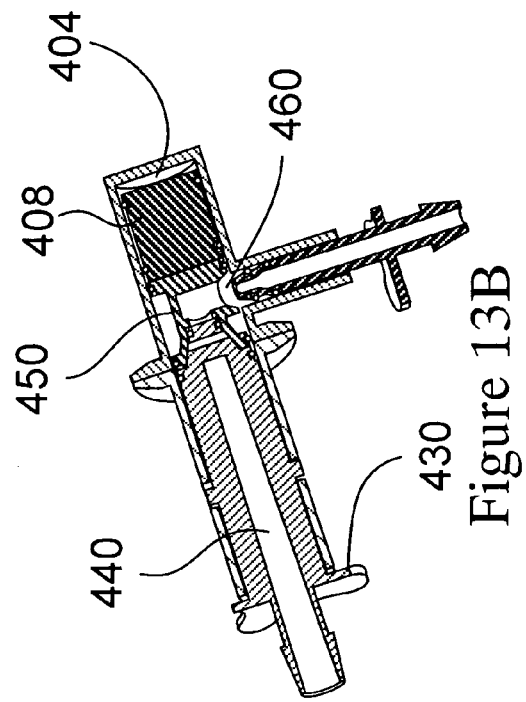

FIGS. 13A–D show the assembly and use of this embodiment. The coupling device 424 containing the garage 450 is mated to the connector 400 such that the garage 450 mates with the plug 408 of the connector 400 as shown in FIG. 13A.

Figure 13D:
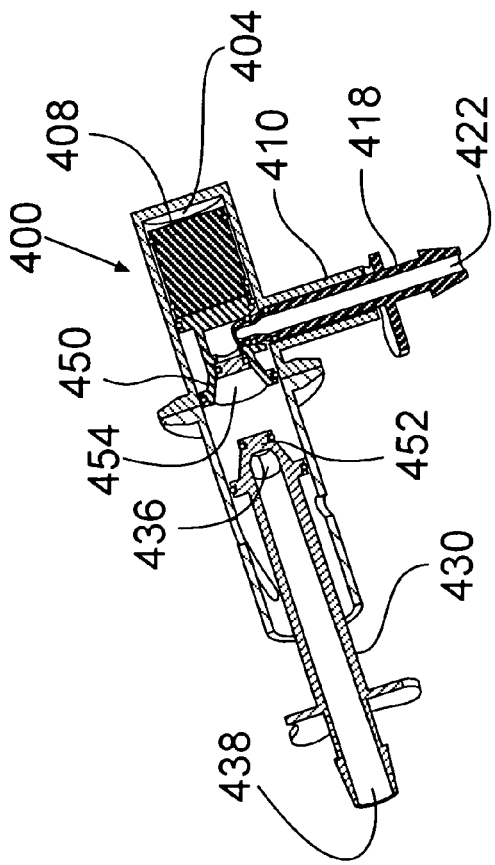
Figure 13B:
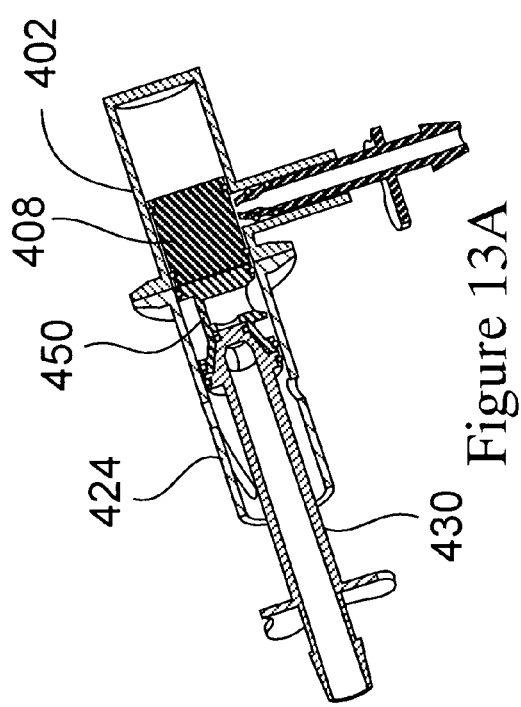

In FIG. 13B the stem 430 is advanced moving the garage 450 and plug 408 into the bore 404 of the top portion 402 to a point where the second bore 460 of the garage 450 aligns with the bore 420 of the stem 418 contained in the bottom portion of the connector 400.

Figure 13C:
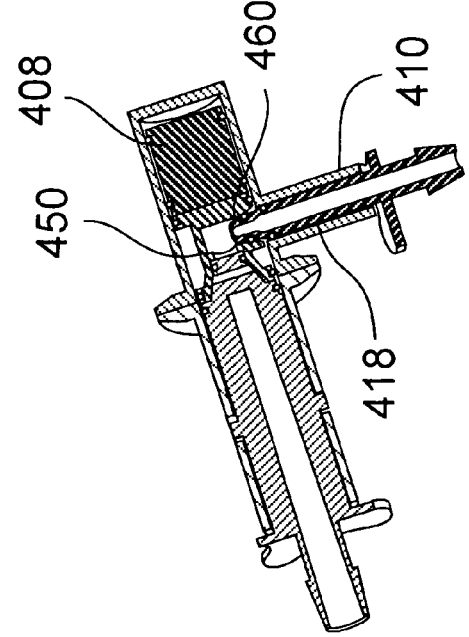

In FIG. 13C the stem 418 of the bottom portion 410 is moved into the second bore 460 of the garage 450 locking it in place with the connector 400 and establishing a fluid communication between the bore 420 of the stem 418 of the bottom portion 410 and the garage 450.

The stem 430 of the coupling device 424 in FIG. 13D is retracted, minus the garage 450 which has been locked in place, exposing the opening 436 in the stem 430 and establishing fluid communication between the second end 438 of the stem 430 of the coupling device 424 and the second opening 422 of the stem 418 of the bottom portion 410 of the connector 400.

As this is device is provided in a sterile condition, i.e. the interior of the system and any component connected downstream of the device is pre-sterilized such as with gamma radiation, ethylene gas or the like and shipped in a sterile condition, some type of use indicator would be helpful so one knows when a system has been used and should therefore be replaced. The use of shrink-wrap protective packaging and the like to indicate an unused sterile condition may also be used.

The present invention provides a sterile connecting device for fluid transfer. It may be single actuation (one open one close) or it may be multiple actuations with a single sterile connection (multiple openings and closings so long as the sterile connection upstream and downstream is maintained). Additionally, with the use of multiple seals or seals of long length, one is able to ensure that the sterility of the device is maintained even with multiple actuations.

The device is simple to assemble and use and eliminates the need for steam sterilization after assembly or the removal of non-sterile membranes and the puncturing of a septum that may cause the formation of particles in the fluid stream.

We claim:

1. A sterile connection device comprising a connector having two openings, each opening being sealed from the environment so as to form a sterile environment within the connector, at least one opening being sealed from the environment by a first sterile barrier plug, the connector also comprising a port capable of three positions, a first closed position, a second partially opened position and a third open position, wherein the port of the connector in its closed position has a portion supporting the sterile plug and maintaining it in its position within the connector, the port has a first opening and a second opening wherein the first opening is capable of containing two or more sterile barrier plugs, at least one coupling device, the coupling device being comprised of a body having an inlet and an outlet, a stem contained within the body and capable of moving at least linearly through the body between a first and second stem position, the outlet being sealed from the environment by a sterile barrier plug and the inlet being sealed to a presterilized component, the outlet of the at least coupling device being attached to either the inlet or outlet of the connector.

2. The device of claim 1 wherein both openings of the connector is sealed by a sterile barrier plug and a coupling device is attached to each of the two openings of the connector.

3. The device of claim 1 wherein an area of the port surrounding each opening contains a liquid tight seal.

4. The device of claim 1 wherein an area of the port surrounding each opening contains a liquid tight seal in the form of an O-ring retained within a performed channel.

5. The device of claim 1 wherein an area of the port surrounding each opening contains a liquid tight seal in the form of a formed in place resilient gasket retained within a performed channel.

6. A process of forming a sterile to sterile connection comprising (a) taking a connector having two openings, each opening being sealed from the environment so as to form a sterile environment within the connector, at least one opening being sealed from the environment by a first sterile barrier plug, the connector also comprising a port capable of three positions, a first closed position, a second partially opened position and a third open position, wherein the port of the connector in its closed position has a portion supporting the sterile plug and maintaining it in its position within the connector, the port has a first opening and a second opening wherein the first opening is capable of containing two or more sterile barrier plugs, (b) attaching at least one coupling device to an opening of the connector containing the sterile barrier plug, the coupling device having a body having an inlet and an outlet, a stem contained within the body and capable of moving at least linearly through the body between a first and second stem position, the outlet being sealed from the environment by a sterile barrier plug and the inlet being sealed to a presterilized component, (c) moving the port to the second partially opened position to align the first opening with the sterile barrier plugs of the connector and the coupling device, (d) moving the plugs of the connector and the coupling into the first opening of the port and (e) moving the port to the third open position to align the second opening with the outlet of the coupling device so as to establish fluid communication between the coupling device and the connector.

7. The process of claim 6 further comprising (f) moving the stem of the coupling device through the second opening of the port of the connector to form a sterile pathway.

8. The process of claim 6 wherein the movement of the port in steps (c–e) is linear.

9. A sterile connection device comprising a connector having two openings, an inlet and an outlet, each opening being sealed from the environment so as to form a sterile environment within the connector, the outlet being sealed to a sterile downstream component, the inlet being sealed from the environment by a first sterile barrier plug, the connector also comprising a port capable of three positions, a first closed position, a second partially opened position and a third open position, wherein the port of the connector in its closed position has a portion supporting the sterile plug and maintaining it in its position within the connector, the port has a first opening and a second opening wherein the first opening is capable of containing two or more sterile barrier plugs, at least one coupling device attached to the inlet of the connector, the coupling device being comprised of a body having an outlet for the device, a stem contained within the body and capable of moving at least linearly through the body between a first and second stem position, the stem containing an inlet to the device at a location distal from the outlet of the device, the outlet being sealed from the environment by a sterile barrier plug and the inlet being sealed to a presterilized component.

10. A process of forming a sterile to sterile connection comprising (a) taking a connector having two openings, each opening being sealed from the environment so as to form a sterile environment within the connector, at least one opening being sealed from the environment by a first sterile barrier plug, the connector also comprising a port capable of three positions, a first closed position, a second partially opened position and a third open position wherein the port of the connector in its closed position has a portion supporting the sterile plug and maintaining it in its position within the connector, the port has a first opening and a second opening wherein the first opening is capable of containing two or more sterile barrier plugs, (b) attaching at least one coupling device to the opening of the connector containing the sterile barrier plug, the coupling device having a body having an inlet and an outlet, a stem contained within the body and capable of moving at least linearly through the body between a first and second stem position, the outlet being sealed from the environment by a sterile barrier plug and the inlet being sealed to a presterilized component, (c) rotating the port to the second partially opened position so as to align the first opening of the port with the sterile plugs of the connector and coupling device, (d) moving the plugs of the connector and the coupling into the first opening of the port and (e) rotating the port to the third open position so as align the second opening of the port with the outlet of the coupling device so as to establish fluid communication between the coupling device and the connector.

11. The process of claim 10 further comprising (f) moving the stem of the coupling device linearly through the second opening of the port of the connector to form a sterile pathway.

* * * * *